United States Patent [19]

Kohler et al.

[11] Patent Number: 4,514,509

[45] Date of Patent: Apr. 30, 1985

[54] METHOD FOR THE DIAGNOSIS OF LEGIONNAIRES' DISEASE

[75] Inventors: Richard B. Kohler; Arthur C. White, both of Indianapolis, Ind.

[73] Assignee: Indiana University Foundation, Bloomington, Ind.

[21] Appl. No.: 304,274

[22] Filed: Sep. 21, 1981

[51] Int. Cl.³ .................. G01N 33/56; C12Q 1/20
[52] U.S. Cl. .................. 436/518; 436/531; 436/545; 436/547; 436/804; 436/811; 435/7; 435/29; 435/34; 435/35
[58] Field of Search .............. 424/1; 436/518, 545, 436/547, 531, 804, 811; 435/5, 9, 7, 29, 34, 35

[56] References Cited

PUBLICATIONS

Farshy et al., *Detection of Antibodies to Legionnaire's Disease Organism by Microagglutination and Micro-Enzyme-Linked Immunosorbent Assay Tests,* J. Clin. Microbiol., vol. 7, 327 (1978).

Kohler et al., *Rapid Diagnosis of Pseudomonas Urinary Tract Infections by Radioimmunoassay,* J. Clin. Microbiol., vol. 9, 253–254 (1979).

Tregear et al., *Solid Phase Radioimmunoassay in Antibody Coated Tubes,* Science 158:1570–1571 (1967).

Baumann et al., *Solid Phase Radioimmunoassay for Human Growth Hormone,* Immunochemistry 6:699–713 (1969).

Ling et al., *Prevalence of Hepatitis B Virus Antigen as Revealed by Direct Radioimmune Assay with 125I–Antibody,* J. Immunol. 109:834–841 (1972).

Berdal et al., *Detection of Legionella pneumophila Antigen in Urine by Enzyme-Linked Immunospecific Assay,* J. Clin, Microbiol, vol. 9, 575–576 (1979).

Tilton, *Legionnaire's Disease Antigen Detected by Enzyme-Linked Immunosorbent Assay,* Ann. Int. Med., vol. 90, 697–698 (1979).

Chard, Radioimmunoassay and Related Techniques, North-Holland Pub. Co., Amsterdam, 1978, p. 303.

Mangiafico et al., J. Clin. Microbiol., 13(5):843–845 (1981).

Johnson et al., Chemical Abstracts, vol. 91 (1979) #3720Z.

*Primary Examiner*—Christine M. Nucker
*Attorney, Agent, or Firm*—Kirkland & Ellis

[57] ABSTRACT

A rapid, sensitive, and specific method for diagnosing Legionnaires' disease through the detection of antigens excreted by the patient and a method for preparing anti-Legionella immunoglobulin G for use in such diagnostic method.

10 Claims, No Drawings

METHOD FOR THE DIAGNOSIS OF LEGIONNAIRES' DISEASE

BACKGROUND OF THE INVENTION

1. Field of the Invention

This invention relates to the diagnosis of pneumonias and more particularly to the detection of *Legionella pneumophila* in humans.

2. Description of the Prior Art

*Legionella pneumophila* causes an estimated 1% to 2% of sporadic pneumonias, 4% to 11% of diagnostically difficult pneumonias resembling viral or mycoplasma pneumonia, and, in some hospitals, a significant fraction of nosocomial pneumonias. Currently, the diagnosis of *Legionella pneumophila* pneumonia requires demonstration of specific seroconversion, growth of the organisms from appropriate specimens, or demonstration of organisms in clinical specimens by direct fluorescent (DF) antibody stains. Of the three diagnostic metods, only the DF antibody method is rapid; but it detects *Legionella pneumophila* antigen in only 24% to 75% of those persons known to have Legionnaires' disease. In cases in which the sputum DF antibody is negative, or coughed sputum cannot be obtained, examination of sputum obtained by transtracheal aspiration, lung fluid obtained by lung aspiration, or lung tissue obtained by biopsy may be required. Patients, particularly those unable to produce sputum, will benefit from an alternative noninvasive rapid diagnostic test for Legionnaires' disease, provided that such test is sufficiently specific and sensitive.

Earlier studies by Tilton, *Legionnaires' Disease Antigen Detected by Enzyme-Linked Immunoabsorbent Assay*, 90 Ann. Intern. Med. 697 (April 1979), and by Berdal, Farshy and Feely, *Detection of Legionella pneumophila Antigen in Urine by Enzyme-Linked Immunospecific Assay*, 9 J. Clin. Microbiol. 601 (1981), suggested the potential diagnostic utility of an enzyme-linked immunosorbent assay for the detection of *Legionella pneumophila* antigen. However, both studies were very preliminary, and both suffer fromm low sensitivity (i.e. the number of patients found to have Legionnaires' disease was comparatively low when contrasted with the number known to have the disease). The method employed by Tilton also suffers from cross-reactivity with various organisms in the urine sample other than *Legionella pneumophila* antigen. Neither the Tilton nor the Berdal et al method discloses the use of radioimmunossay techniques.

Accordingly, it is the principal object of the present invention to provide an improved rapid, sensitive and specific means for detecting Legionnaires' disease.

A further object of the present invention is to provide a noninvasive means for detecting Legionnaires' disease.

Another object of the present invention is to minimize the number of tests falsely indicating the presence of Legionnaires' disease.

SUMMARY OF THE INVENTION

In accordance with the subject invention, the foregoing objects have been achieved with an improved method for the diagnosis of Legionnaires' disease comprising measuring the radiation emitted from a test sample surface coated with, firt, a layer substantially free of anti-Legionella immunoglobulin G adsorptive sites but which is capable of binding *Legionella pneumophila* antigen; next, a layer of a test sample obtained from a donor-patient; and finally a layer of isotopically-labelled anti-Legionella immunoglobulin G.

DETAILED DESCRIPTION OF THE PREFERRED EMBODIMENTS

Broadly described, this invention utilizes a surface coated with anti-Legionella immunoglobulin G (hereinafter "IgG"), a test sample obtained from a donor-patient and isotopically-labelled anti-Legionella IgG. The surface on which the layers are formed may be a glass, plastic, or other synthetic polymer tube, disk, jar, plate, container, ball, stick, membrane, or other surface, but preferably is a polystyrene tube.

The anti-Legionella IgG adsorbs to the test surface. A blocking agent, preferably Bovine serum albumin may then be added to occupy any adsorption sites not already occupied so as to produce a surface which is substantially free of anti-Legionella IgG adsorption sites but which is capable of binding *Legionella pneumophila* antigen. Background radiation is thereby minimized by preventing radioiodinated anti-Legionella IgG, added later, for adsorbing to the test surface. The layer is applied by incubating at a temperature in the range of about 22° C. to 45° C., but preferably about 37° C., for about 20 to 1000 minutes, but preferably about 60 minutes, then aspirating and rinsing, thereby forming a solid-phase layer.

The test sample, which can be any bodily fluid including blood, sputum, urine pleural fluid, pus, or other body fluid, but preferably urine is added next. The test sample coated surface is then incubated, thereby binding any *Legionella pneumophila* antigen present in the sample to the anti-Legionella IgG layer already present. Aspiration and rinsing again produces a solid-phase layer.

Finally, an isotopically-labelled anti-Legionella IgG, preferably radioiodinated anti-Legionella IgG, is added and the triple-coated surface is incubated at a temperature in the range of about 4° C. to 45° C., but preferably about 37° C., for about 20 to 1500 minutes, but preferably about 60 minutes, then aspirated and rinsed. The isotopically-labelled anti-Legionella IgG is bound only to *Legionella pneumophila* antigen present in the test sample. Unbound isotopically-labelled anti-Legionella IgG is removed by the aspiration and rinsing. As a result, the radiation emitted from the resulting surface is proportional to the presence of the *Legionella pneumophila* antigen and detection of the radiation thus permits rapid detection of the presence of *Legionella pneumophila* antigen in the donor-patient.

Anti-Legionella IgG employed in the foregoing method may be produced by inoculating a culture medium, preferably Mueller-Hinton agar supplemented with 1% Iso VitaleX and 1% hemoglobin, with *Legionella pneumophila*, preferably serogroup 1 *L. pneumophila*, Philadelphia 1 strain. The inoculated culture medium is then incubated for about 3 to 14 days, but preferably about 7 days, and preferably in sealed carbon dioxide permeable containers, which retain moisture but permit a carbon dioxide enriched atmosphere, in a carbon dioxide incubator at a temperature in the range of about 22° C. to 45° C., but preferably about 35° C.

The resulting Legionella organisms are then physically removed from the culture medium, preferably by scraping or gentle rubbing. They are added to a buffer, preferably a buffer of the type phosphate-buffered saline, preferably with a PH of about 7.2. The suspended Legionella organisms are then inoculated into a mammal, such as a goat or rabbit, but preferably a rabbit and preferably subcutaneously and intrasmuscularly at multiple injection sites and preferably twice weekly for two weeks then once weekly for two weeks. The mammal is then phlebotomized no earlier than about 6 weeks after the onset of immunization but before the death of the mammal, preferably about 16 months after the first immunization. The anti-Legionella IgG is then separated from the serum, preferably through Sephadex G200 or dimethylaminoethyl cellulose.

Isotopically-labelled anti-Legionella IgG is then produced by allowing a radioisotope, preferably $^{125}I$ to react with the anti-Legionella IgG, preferably by mixing Chloramine-T, anti-Legionella IgG and $^{125}I$ for about 8 to 11 minutes, but preferably about 10 minutes at which time the reaction is terminated, preferably by the addition of sodium metabisulfite. The isotopically-labelled anti-Legionella IgG is then separated from the unbound radioisotope, preferably in a Sephadex G25 column or by dialysis.

The practice of the present invention is illustrated by the following examples.

EXAMPLE I

Polystyrene tubes (10×70 mm) are coated with anti-Legionella IgG by incubating 0.1 ml of a 20 ug/ml IgG solution in 0.01M Tris (hydroxymethyl)aminomethane hydrochloride, pH 7.0, at 37° C. for one hour. After aspirating and rinsing, 0.1 ml of 5% bovine serum albumin in 0.01M tris (hydroxymethyl)aminomethane hydrochloride, pH 7.0, is next incubated similarly to occupy any remaining protein adsorption sites.

Next, 0.1 ml of a test urine specimen from a patient being tested for Legionnaires' disease is added to the tubes, incubated again at 37° C. for one hour, then aspirated and rinsed.

The solid-phase sandwich is completed by adding 0.1 ml of radioiodinated anti-Legionella IgG incubating at 37° C. for one hour, then aspirating and rinsing.

The tubes are then assayed in a gamma counter. As a cross-check and to increase the accuracy of the method of the present invention, triplicate tubes may be tested for each urine sample. Control urine samples selected daily from patients with negative urine cultures who are known not to have Legionnaires' disease are also tested. The mean of each test urine's triplicate tubes is divided by the mean of the control urines obtained on the day of the test to determine the final assay ratio. The presence of Legionnaires' disease is indicated by a ratio of 2.0 or greater.

EXPERIMENTAL EVALUATIONS

Ninety-two urine specimens from 59 patients were tested in the radioimmunossay. Of these, 56 specimens were from 33 patients who met the independent criteria for Legionnaires' disease. Sixteen other patients could not be classified with confidence. Finally, 8 specimens were obtained from 5 patients from whom little information was available.

The results of the radioimmunoassay had a high correlation to the independently determined presence of Legionnaires' disease. Specifically, the results indicate that specimens collected on or before day one of erythromycin therapy will be positive in about 80% of Legionnaires' disease patients tested. By day 4, this declines to 52% by day 7, to 37%; and by day 14, to 7%.

EXAMPLE 2

Anti-Legionella IgG

The immunogen is made by innoculating Mueller-Hinton agar, supplemented with 1% hemoglobin and 1% IsoVitaleX (Baltimore Biological Laboratories Cockeysville, Md.) with the fifth-day growth in Mueller-Hinton broth, supplemented with 3% Fildes enrichment (Difco Laboratories, Detroit, Mich.) and 2% IsoVitaleX, of serogroup 1 *L. pneumophila*, Philadelphia 1 strain (Center for Disease Control). After 7 days of incubation in sealed carbon dioxide-permeable plastic bags in a 5% to 10% carbon dioxide incubator at 35° C., the organisms are scraped from the agar, added to phosphate-buffered saline, pH 7.2, and heated in an autoclave at 101° C. for one hour. The cells are removed by centrifugation, resuspended in 10 ml of phosphate-buffered saline per 0.5 ml of packed cells, repacked by centrifugation, then placed at 4° C. for 14 days. For immunization the packed organisms are resuspended, then mixed with an equal volume of complete Freund's adjuvant. The immunogen is injected into a rabbit subcutaneously and intramuscularly at multiple injection sites twice weekly for 2 weeks then once weekly for 2 weeks. Thereafter, periodic booster immunizations were made. The antiserum is obtained by phlebotomizing the rabbit 16 months after the onset of immunization. It is then eluted through G200 Sephadex (Pharmacia Fine Chemicals, Piscataway, N.J.) to obtain anti-Legionella IgG. In order to produce Radio-iodinated anti-Legionella IgG, Chloramine-T, anti-Legionella IgG and $^{125}I$ are mixed and allowed to react for 10 minutes at which time the reaction is terminated by the addition of sodium metabisulfite. The radioiodinated anti-Legionella IgG is then separated from the unbound $^{125}I$ in a Sephadex G25 column.

We claim:

1. A method for the detection of antigens of the organism *Legionella pneumophila* in a human donor-patient, which comprises the steps of:
   (a) inoculating a culture medium with *Legionella pneumophila* thereby forming a Legionella innoculated culture medium;
   (b) incubating said Legionella inoculated culture medium thereby producing *Legionella pneumophila* organisms;
   (c) removing, incubating and heating by auto-claving said Legionella organisms in a buffer thereby forming suspended Legionella organisms;
   (d) inoculating a mammal with said suspended Legionella organisms thereby producing anti-Legionella immunoglobulin G in said mammals;
   (e) recovering anti-Legionella immunoglobulin G from the mammal;
   (f) isotopically labelling at least some of the anti-Legionella immunoglobulin G thereby forming isotopically-labelled anti-Legionella immunoglobulin G;
   (g) forming a layer capable of binding *Legionella pneumophila* antigen but substantially incapable of adsorbing anti-Legionella immunoglobulin G on a test surface thereby forming an antigen binding test surface;

(h) depositing a test sample obtained from a donor-patient on the antigen binding test surface thereby forming a test sample-treated test surface;

(i) forming a layer of the isotopically-labelled anti-Legionella immunoglobulin G on said test sample-treated test surface thereby forming a radioactively labelled surface in which the emitted radiation is proportional to the presence of *Legionella pneumophila* antigen; and (j) measuring the radiation emitted by the radioactively-labelled surface thereby obtaining a test value indicative of the presence of *Legionella pneumophila*.

2. The method of claim 1 wherein said test sample comprises urine.

3. The method of claim 1 wherein the antigen binding test surface comprises a layer of the anti-Legionella immunoglobulin G produced according to the method of steps a–e of claim 1 treated with a blocking agent.

4. The method of claim 1 wherein said radiation is measured in a gamma counter.

5. The method of claim 1 wherein said layers are formed by incubating, aspirating and rinsing.

6. The method of claim 1 wherein the mammal is a rabbit.

7. The method of claim 1 wherein isotopically-labelled anti-Legionella immunoglobulin G is formed by reacting said anti-Legionella immunoglobulin G with a radioisotope.

8. The method of claims 7 or 1 wherein said isotopically-labelled anti-Legionella immunoglobulin G comprises radioiodinated anti-Legionella immunoglobulin G.

9. The method of claim 7 wherein said radioisotope comprises $^{125}I$.

10. The method of claim 3 wherein said blocking agent comprises bovine serum albumin.

* * * * *